Sept. 25, 1956 L. MAIN Plant Pat. 1,521
OLIVE TREE
Filed Nov. 18, 1955
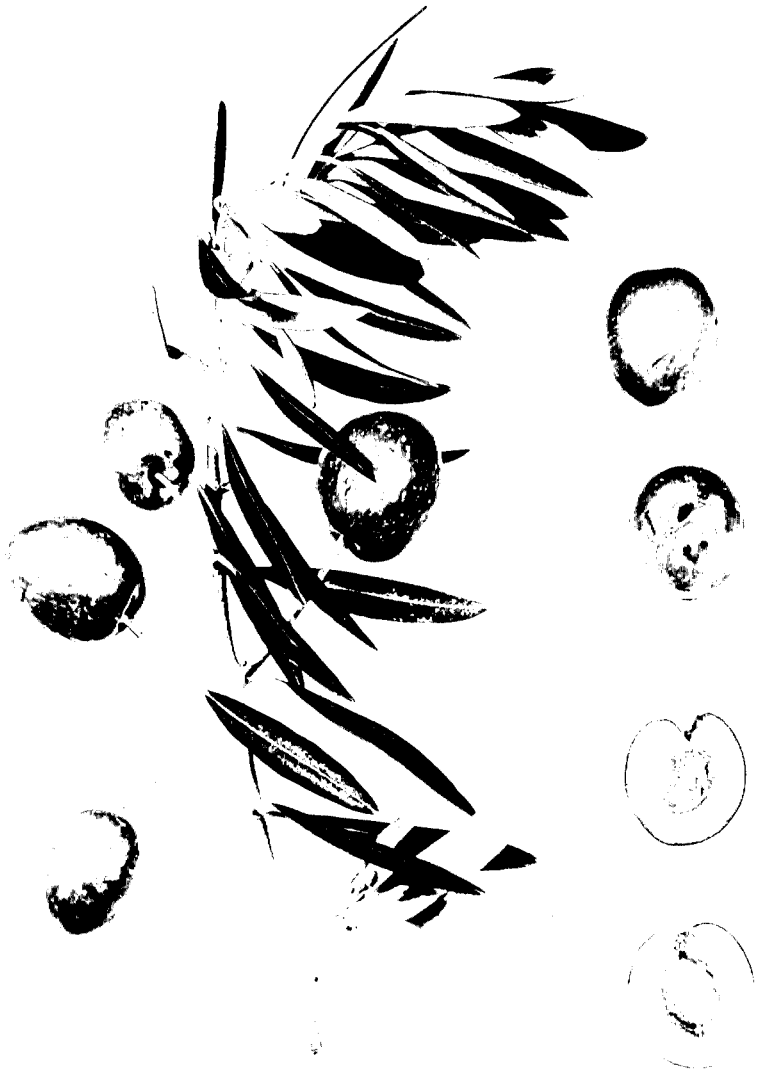
Inventor.
Lloyd Main
By: Cobb & Cobb
Attorneys.

United States Patent Office

Plant Pat. 1,521
Patented Sept. 25, 1956

1,521

OLIVE TREE

Lloyd Main, Visalia, Calif.

Application November 18, 1955, Serial No. 547,875

1 Claim. (Cl. 47—62)

The present invention relates to a new and distinct variety of olive tree which was originally discovered by me as a newly found seedling on my cultivated ranch near Ivanhoe, in Tulare County, California.

My attention was initially attracted to the new variety by its more bushy and more spreading habit of growth than that of other usual olive varieties which I was growing on my ranch, and accordingly, I took steps to preserve and observe the new seedling. The results of my continued observations of the original seedling, and of asexual reproductions thereof which were produced by me by grafting, as performed on my ranch, have fully demonstrated and established that not only the bushy and spreading habit of growth is fixed and comes true to form, but also, that the new seedling is characterized by other unique and desirable features, the most outstanding of which are as follows:

(1) The size of the tree, as well as the general aspect of the foliage and fruit, fall intermediate those of the "Manzanillo" and "Sevillano" varieties (both unpatented), with a greater tendency to simulate the 'Manzanillo" variety, except that the fruit size approaches that of "Sevillano," without the tendency of the latter towards "shot" berries;

(2) The leaves are narrower, smaller, more pointed and darker in color than most conventional olive varieties;

(3) Its relatively heavy fruit production generally equals that of the "Manzanillo" variety, but the fruit matures about midway between that of the "Manzanillo" and "Sevillano" varieties, which is a distinct advantage from a commercial standpoint, particularly in the fall season;

(4) The relatively large size of the fruit, and the tough skin thereof which is more resistant to bruises;

(5) The free to semi-free character of the pit or stone, with the pit being of average size and thus resulting in a larger portion of meat in proportion to the size of the pit;

(6) The absence of any tendency of the pit or stone to split during canning or other processing; and (7) The retention of firmness of the fruit when processed or canned, and the excellent flavor, good keeping and shipping qualities of the fruit, making the same particularly useful when processed as dark ripe or green ripe olives or green Spanish pickle.

The foregoing characteristics represent a new, unique and desirable combination, and although the parentage of my new variety is not definitely known to me, I am convinced that it is a new variety and is distinct from all other varieties.

The accompanying drawing shows typical specimens of the foliage and fruit of my new variety, with both the upper side and the under side of the foliage being depicted, and with the fruit shown in various elevations as well as in longitudinal section, one of the fruit sections containing the pit or stone and the other fruit section exposing the pit cavity, all as depicted in color as nearly true as it is reasonably possible to make the same in a color illustration of this character.

The following is a detailed description of my new variety, with color terminology in accordance with Koster's Color Guide, except where general color terms of ordinary dictionary significance are obvious:

Parentage: Newly found seedling of unknown parentage.

Propagation: Holds its distinguishing characteristics through succeeding propagations by grafting.

Locality where grown and observed: Near Ivanhoe, in Tulare County, California.

Dates of picking: From October 1st to October 20th.

Tree: Medium size; bushy; spreading; dense; round; hardy; moderately productive; regular bearer.

*Trunk.*—Stocky; smooth.

*Branches.*—Stocky; smooth. Color—near Ashy Grey, Plate No. 99. Lenticels—numerous; medium size.

*Leaves.*—Lanceolate; acutely pointed; smooth; with general leaf appearance somewhat between that of the varieties "Manzanillo" and "Sevillano." Size—medium. Length—from 1¾ inches to 2½ inches. Width—from 5/16 inch to ½ inch. Color—upper side: somewhat darker than Taxus Green, Plate No. 81, under side: somewhat lighter than Artichoke Green, Plate No. 72, and between Artichoke Green, Plate No. 72 and Pearl Grey, Plate No. 100. Margin—entire. Petiole—medium. Glands—normal. Stipules—none.

Flowers: Normal and typical of conventional olive varieties.

Fruit: Maturity for canning—October 6th to October 30th.

*Size.*—From medium to large. Axial diameter—about 1 3/16 inches. Diameter in suture plane—1 5/16 inch. Transverse diameter at right angle to suture plane—⅞ inch.

*Form.*—Uniformly symmetrical; ovoid; approximately midway between typical "Manzanillo" and "Sevillano" fruit, although tending toward "Manzanillo."

*Suture.*—Indistinct.

*Ventral surface.*—Rounded.

*Cavity.*—Rounded. Depth—⅛ inch. Breadth—3/16 inch. Marking—from indistinct to two opposing slight depressions.

*Base.*—Rounded.

*Apex.*—Short. Pistil point—oblique.

*Stem.*—Variable length, but average medium length; no adherence to stone. Color—between Sulphury White, Plate No. 3 and Yellowish Green, Plate No. 73.

*Skin.*—Medium thickness; tough; tenacious to flesh; no tendency to crack; no down. Color—from near Moss Green, Plate No. 76 with numerous lighter dots of near Lettuce Green, Plate No. 74, to intense purple or black when ripe.

*Flesh.*—Color—shading from near Lettuce Green, Plate No. 74 next to skin, to near Sulphury White, Plate No. 3 next to stone or pit. Texture—firm. Fibers—none. Ripens—evenly. Flavor—excellent; similar to "Manzanillo" when processed. Aroma—normally typical of conventional olives. Eating quality—excellent.

Stone: From semi-free to free; when adherent, it adheres over entire surface, but without fibrous attachments.

*Size.*—From medium to small. Length—about ⅝ inch. Breadth—about 7/16 inch. Thickness—about ½ inch.

*Form.*—From elliptical full to slightly curved.

*Base.*—From straight to slightly oblique. Hilum—broad. Apex—rounded.

*Sides.*—Equal; slightly flattened.

*Surface.*—Rough, with numerous prominent furrows crossing it longitudinally and sometimes fairly well-defined the entire length, but sometimes divided and warty.

*Ridges.*—Rounded or jagged throughout.

*Pits.*—Elongate; angular.

*Tendency to split.*—From slight to none.

*Color.*—Between buff, Plate No. 90 and tan, Plate No. 91; typical of conventional varieties.

Use: Canning; makes excellent dark ripe and green ripe olives, as well as excellent green Spanish pickle.

Keeping quality: Good.

Shipping quality: Good.

General Aspect: Both foliage and fruit characteristics fall approximately midway between those of "Manzanillo" and "Sevillano," with a greater tendency to simulate "Manzanillo," except that the fruit size approaches that of "Sevillano," without the tendency of the latter toward "shot" berries.

I claim:

A new and distinct variety of olive tree, substantially as herein shown and described, characterized particularly as to novelty by its bushy and spreading habit of growth, its relatively narrow, small, pointed and dark green leaves, its relatively heavy fruit production, said fruit having a maturity approximately midway between that of the varieties "Manzanillo" and "Sevillano," the relatively large size of the fruit while having pits of average size with consequent greater proportion of edible flesh, the absence of any tendency towards "shot" berries, the tough skin of the fruit and consequent resistance thereof to bruises, the comparative freedom of the pit from any tendency to split during canning, the substantially freestone habit of the fruit, the retention of firmness of the fruit when processed or canned, and the excellent flavor and good keeping and shipping qualities of the fruit.

No references cited.